United States Patent
Danks et al.

[19]

[11] Patent Number: 5,868,773
[45] Date of Patent: Feb. 9, 1999

[54] SHIELDED TROCAR WITH SAFETY LOCKING MECHANISM

[75] Inventors: John K. Danks, Delray Beach, Fla.; Richard V. Mazzola, Bloomfield, N.J.

[73] Assignee: Endoscopic Concepts, Inc., Delray Beach, Fla.

[21] Appl. No.: 480,412

[22] Filed: Jun. 7, 1995

Related U.S. Application Data

[63] Continuation-in-part of Ser. No. 339,897, Nov. 14, 1994, abandoned, which is a continuation of Ser. No. 38,904, Mar. 30, 1993, Pat. No. 5,364,372.

[51] Int. Cl.[6] ........................................ A61B 17/34
[52] U.S. Cl. ........................................ 606/185; 604/264
[58] Field of Search ........................................ 606/167, 170, 606/185; 604/164, 264

[56] References Cited

U.S. PATENT DOCUMENTS

| 4,931,042 | 6/1990 | Holmes et al. | 606/185 |
| 5,314,417 | 5/1994 | Stephens et al. | 604/264 |

FOREIGN PATENT DOCUMENTS

| 0265193 | 4/1988 | European Pat. Off. | 606/185 |

*Primary Examiner*—Glenn Dawson
*Attorney, Agent, or Firm*—Miller & Martin

[57] ABSTRACT

A trocar is formed from a cannula and an interfitting obturator for penetrating body cavity walls in laparoscopic and endoscopic surgery. The obturator is provided with an improved piercing tip having a pointed blade and an improved locking shield design. The locking mechanism must be actuated before the shield will retract to expose the piercing tip. The shield is located inside the obturator sheath and provides faster coverage of the piercing tip after the body cavity wall has been penetrated. The cannula has an improved thread design to more easily and securely hold the cannula in the incision of the body cavity wall. A one piece inner housing is used in the cannula to reduce the need for welding to prevent gas leakage. The cannula also has improved seals to maintain insufflation of the body cavity and an automatic insufflation valve to facilitate connection to an external gas supply. Reducing fittings may also be used on the cannula to allow the insertion of endoscopic instruments of lesser diameter than the obturator.

19 Claims, 8 Drawing Sheets

SHIELDED TROCAR WITH SAFETY LOCKING MECHANISM

The present application is a continuation-in-part of abandoned application Ser. No. 08/339,897 filed Nov. 14, 1994, now abandoned which is a continuation of application Ser. No. 08/038,904 filed Mar. 29, 1993 and now U.S. Pat. No. 5,364,372.

BACKGROUND OF THE INVENTION

The present invention relates to a surgical instrument commonly referred to as a trocar, or an obturator and cannula, often used in laparoscopic or arthroscopic surgery. More particularly, the invention relates to new and improved designs for piercing tips, shields, and shield locking mechanisms, seals, and improved stability threads on the cannula through which the piercing tip passes, and the use of an automatic insufflation valve on the cannula.

Many surgical procedures are now being performed with the use of trocars and cannulas. Originally these devices were used for making a puncture and leaving a tube to drain fluids. As technology and surgical techniques have advanced, it is now possible to insert surgical instruments through the cannulas and perform invasive procedures through an opening often less than half an inch in diameter. Previously these procedures required an incision of many inches. By minimizing the incision, the stress and loss of blood suffered by patients is reduced and the patients' recovery times are dramatically reduced.

Surgical trocars are most commonly used in laparoscopic surgery. Prior to use of the trocar, the surgeon will usually introduce a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, pneumoperitoneum is created separating the wall of the body cavity from the internal organs.

A trocar is then used to puncture the body cavity. The piercing tip or obturator of the trocar is inserted through the cannula or sheath and the cannula partially enters the body cavity through the incision made by the trocar. The obturator can then be removed from the cannula and an elongated endoscope or cameras may be inserted through the cannula to view the body cavity, or surgical instruments may be inserted to perform ligations or other procedures.

A great deal of force is often required to cause the obturator to pierce the wall of the body cavity. When the piercing tip breaks through the cavity wall, resistance to penetration ceases and the tip may reach internal organs or blood vessels, with resultant lacerations and potentially serious injury. The creation of the pneumoperitoneum provides some free space within which the surgeon may stop the penetration of the trocar. To provide further protection, trocars have more recently been developed with spring loaded shields surrounding the piercing tip of the obturator. Once the piercing tip of the obturator has completely pierced the body cavity wall, the resistance of the tissue to the spring loaded shield is reduced and the shield springs forward into the body cavity and covers the piercing tip. The shield thereby protects internal body organs and blood vessels from incidental contact with the piercing tip and resultant injury. Trocars including various safety shield designs are described in Yoon, U.S. Pat. No. 4,535,773; Moll, U.S. Pat. No. 4,654,030; and Moll, U.S. Pat. No. 4,601,710.

Once the cannula has been introduced into the opening in the body cavity wall, the pneumoperitoneum may be maintained by introducing gas into the abdominal cavity through the cannula. Various seals and valves have been utilized to allow abdominal pressure to be maintained in this fashion. Maintaining abdominal pressure is important both to allow working room in the body cavity for instruments introduced through the cannula, and to provide free space for the puncturing of the body cavity wall by one or more additional trocars as may be required for some procedures.

While the existing trocars and cannulas have proven useful, several disadvantages remain. The force required to cause the piercing tip to penetrate a body cavity wall is often so great that some physicians must strain to use the trocar with resulting loss of control over the depth of penetration of the instrument. In addition, the existing shield mechanisms require that the obturator's piercing tip have completely penetrated the body cavity wall before the shield springs forward to cover the obturator tip. The delay in covering the piercing tip exposes the patient to unnecessary risk of internal laceration.

Also, the cannula providing communication through the body cavity wall has a tendency to slide in and out of the incision in the wall, particularly when the surgeon is introducing or removing various instrumentation. Finally, the locking mechanisms for existing trocars have proved unwieldy often with the result that an actuated trocar is left unattended and posing a hazard to persons nearby when it is moved. Therefore, a need exists for an improved apparatus for performing laparoscopic and similar surgical procedures.

SUMMARY OF THE INVENTION

Accordingly, it is the primary object of the invention to provide a safer trocar for piercing body cavity walls and an improved cannula for communication through body cavity walls.

It is also an object of the invention to provide an improved shield design which will provide faster coverage of the obturator's piercing tip and which will enter the body cavity wall in such a fashion as to enable a closer fit between the body cavity wall and the cannula.

It is a further object of the invention to provide improved blade designs for the piercing tips of obturators which will permit easier penetration of body cavity walls, with less blade surface to rub against tissue. In preferred form, such blade designs may also accommodate improved shield designs.

It is another object of the invention to provide a cannula which may be inserted in an opening in a body cavity wall and which will seal tightly, will not move substantially relative to the body cavity wall during use, and which may be easily removed after use.

It is another object of the invention to provide a shield locking device so that the shield must be armed by the surgeon before the obturator's piercing tip may be exposed.

It is still another object of the invention to provide a locking mechanism that can be armed and relocked without the necessity of retracting and releasing the shield or separating the obturator from the cannula.

Accordingly, the present invention provides a cannula with external threads to provide stability during use, and through which an obturator may be inserted. To achieve faster shield protection, the shield is located internal to the obturator and is biased to move forward to cover the obturator's piercing tip when the piercing tip penetrates the body cavity wall. The shield is also preferably connected to a locking mechanism so that the shield must be "armed" before it will retract and expose the obturator's piercing tip. To achieve easier penetration of body cavity walls, the obturator's piercing tip is generally comprised of a pointed blade or blades rather than a solid pyramidal or conical shape.

BRIEF DESCRIPTIONS OF THE DRAWINGS

DESCRIPTION OF THE PREFERRED EMBODIMENTS

Figure 1:
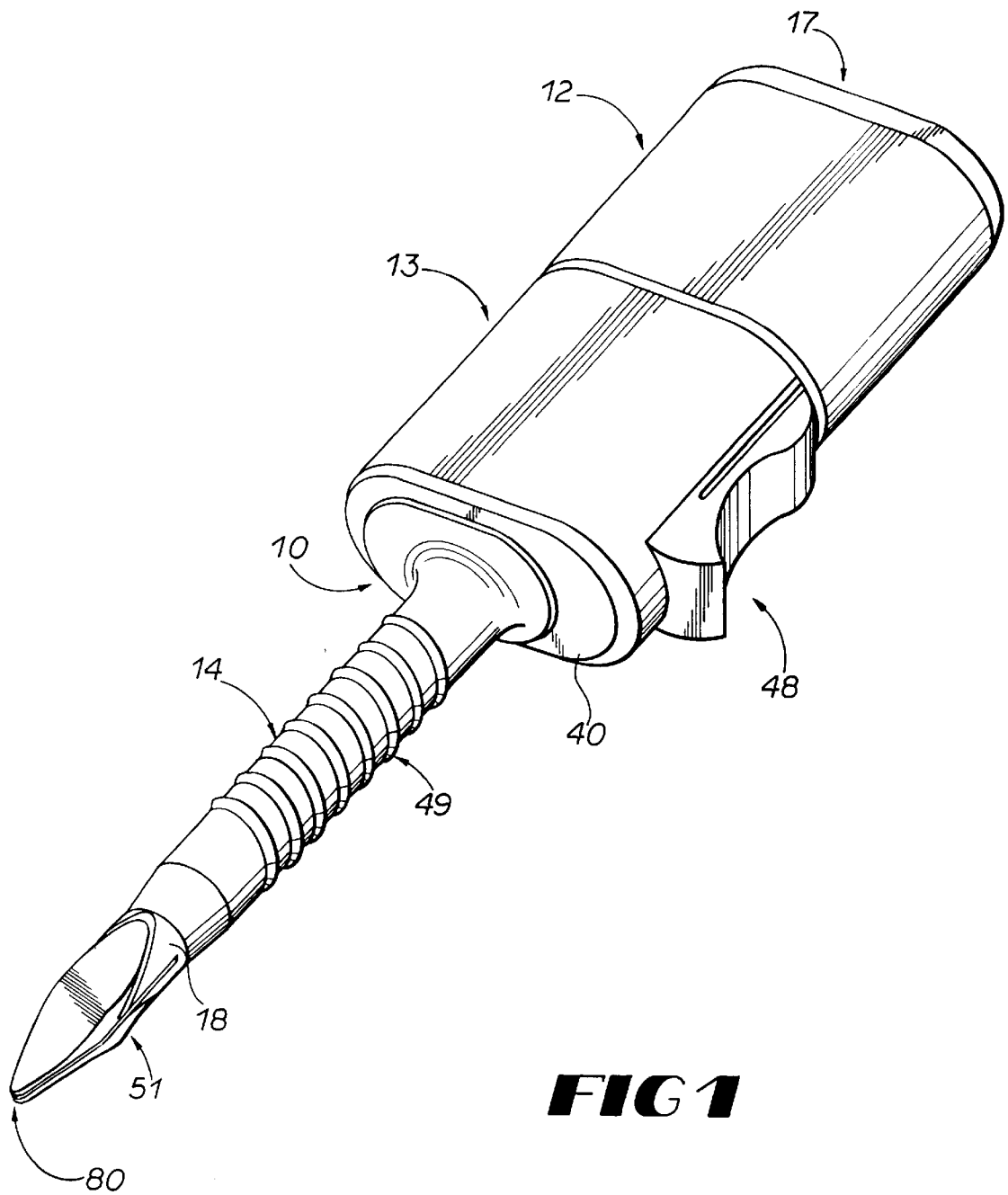
FIG. 1 is a perspective view of a shielded embodiment of the invention.

The invention 10, known as a "trocar" or "obturator and cannula," is illustrated in FIG. 1 with two component parts or subassemblies. The first part is referred to as the obturator 12, while the second part is referred to as the cannula 13. The obturator 12 and cannula 13 are interfitting and as explained below are used together to penetrate a body cavity wall. Once the body cavity wall is penetrated, however, the obturator 12 may be removed and other medical instruments may be introduced into a lumen 19 (shown in FIG. 3C) of the cannula 13.

Figure 2A:
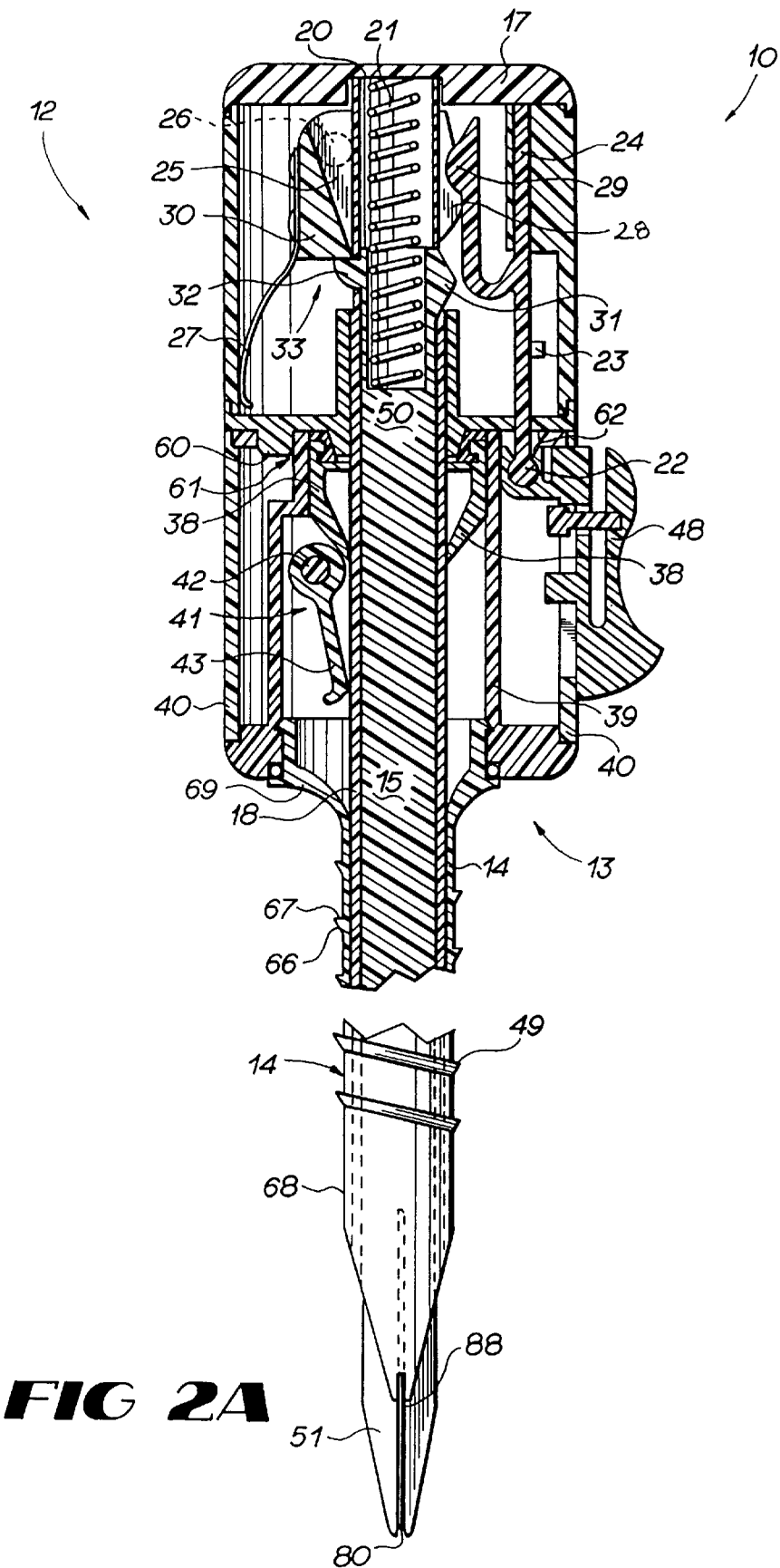
FIG. 2A illustrates a side view of a shielded embodiment of the invention partially in cross-section.
Figure 3B:
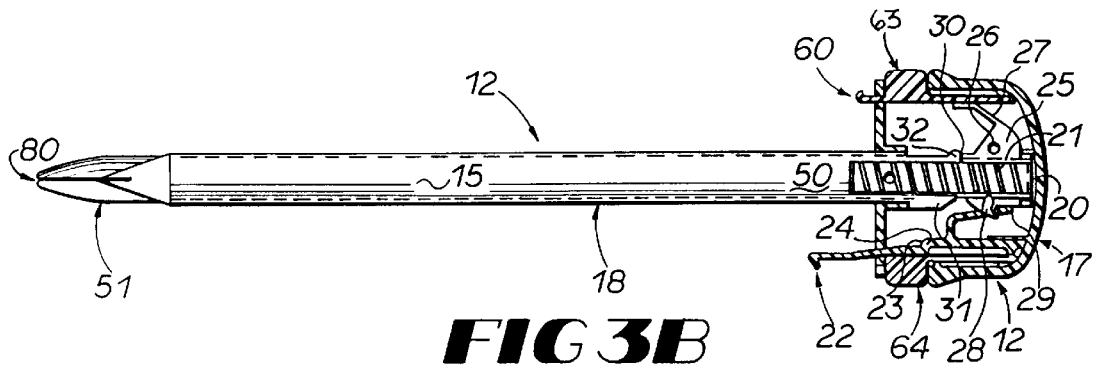
FIG. 3B illustrates a sectional side view of the obturator of the invention shown in FIG. 3A.
Figure 3C:
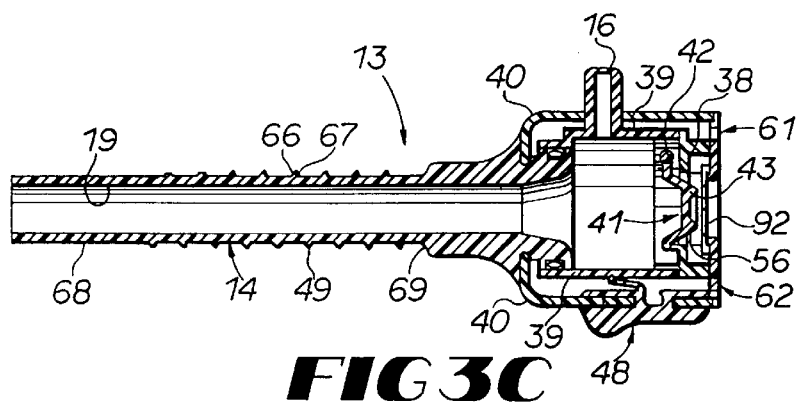
FIG. 3C illustrates a sectional side view of the cannula of the invention shown in FIG. 3A.
Figure 3A:
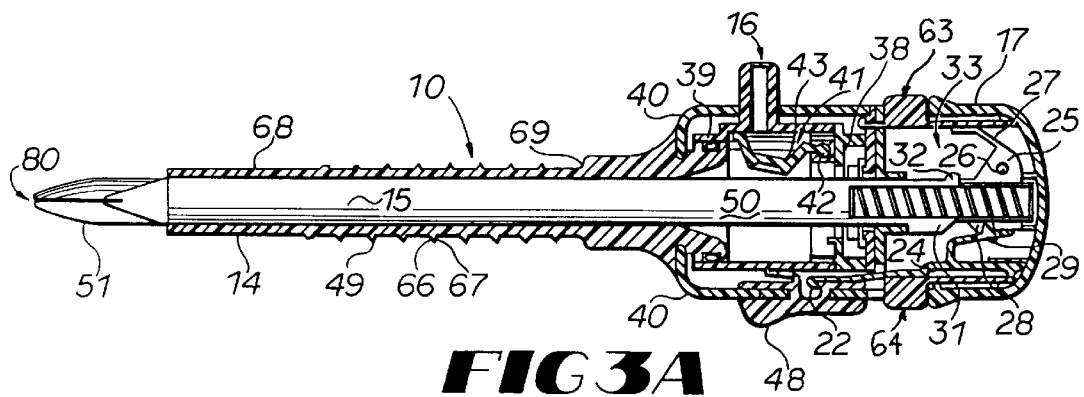
FIG. 3A illustrates a sectional side view of an alternative shielded embodiment of the invention.

A shielded obturator 12 is shown in greater detail in FIGS. 2A, 3A and 3B. The shielded obturator 12 in FIG. 2A includes an obturator housing 17 which forms a grip or handle for the trocar 10. The shielded obturator 12 also includes a hollow obturator sheath 18, the proximal end of which is mounted to the obturator housing 17. The distal end of the obturator sheath 18 is fitted with a piercing tip 80. Housed within the obturator sheath 18 is the shield 15, shown in its extended position with the distal end 51 covering the piercing tip 80. The preferred design of the distal end of the shield is described in applicant's co-pending Ser. No. 08/238,959. The proximal end 50 of the shield 15 is received some distance within the hollow obturator sheath 18 where it is outwardly biased by a biasing means such as the coiled spring 21 interposed between the proximal end 50 of the shield 15 and the inner wall 20 of the obturator housing 17.

Still referring to FIG. 2A, a latch means 33 for locking the shield 15 in the extended position is illustrated. The latch means 33 comprises a biasing means such as the leaf spring 27, a blocking member such as the illustrated pivoting chock 25, an actuation means such as the trigger 48, and a linkage between the actuation means and the blocking means such as the linking member 24. The illustrated latch means 33 operates to keep the shield 15 locked in the extended position except when armed or actuated. To lock the shield 15, a solid portion 30 of the pivoting chock 25 engages with a lug 32 on the proximal end 50 of the shield 15 to prevent the shield 15 from retracting further toward the inner wall 20 of the obturator housing 17 and thereby exposing the piercing tip 80.

In order to permit the shield 15 to be retracted, the latch means 33 must first be armed or actuated. In the embodiment illustrated in FIG. 2A, the distal end 22 of the linking member 24 engages with a trigger 48. When the trigger 48 is depressed and pushed forward toward the piercing tip 80, the linking member 24 is likewise pulled forward. A hook 29 on the proximate end of the linking member 24 is engaged in a cradle 28 on the pivoting chock 25. As the linking member 24 is pulled forward, it causes the pivoting chock 25 to turn on its pivot 26 and thereby rotates the solid portion 30 away from the lug 32 on the proximal end 50 of the shield 15. This arms or actuates the trocar 10.

Figure 2B:
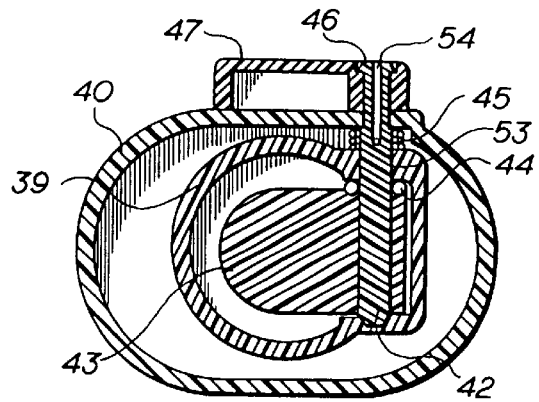
FIG. 2B illustrates a sectional front view of the cannula of the invention shown in FIG. 2A, taken along a line through the flapper valve assembly.
Figure 2C:
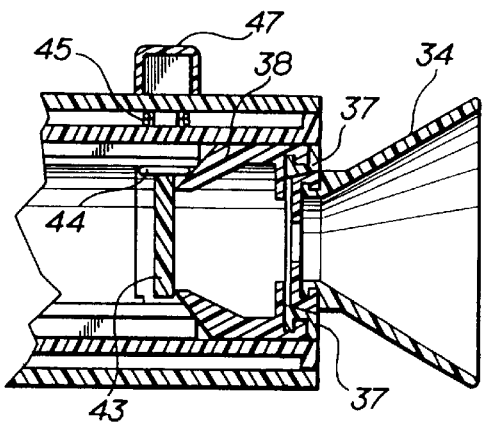
FIG. 2C illustrates a partial sectional top plan view of the cannula of the invention shown in FIG. 2A with a funnel attachment.
Figure 2D:
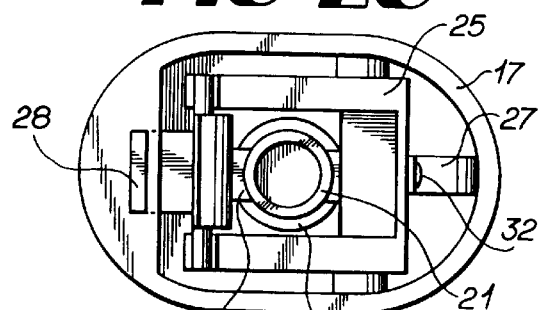
FIG. 2D illustrates a sectional front view of the obturator of the invention shown in FIG. 2A taken along a line through the shield arming and latching mechanism.

As the trigger 48 continues forward, the linking member 24 also travels forward until a stop block 23 halts further movement. When the stop block 23 halts further movement, the linking member 24 is in close proximity to a cam 31 protruding from the proximal end 50 of the shield 15. As soon as the surgeon applies pressure to the trocar 10, the shield 15 is pushed back into the housing 17. The cam 31 on the proximate end 50 and the shield 15 then dislodges the hook 29 of the linking member 24 from the cradle 28 of the pivoting chock 25. A biasing means such as the leaf spring 27 acting on the pivoting chock 25 now causes the solid portion 30 of the pivoting chock 25 to try to return to its original locking position. If the shield 15 is even partially retracted, the pivoting chock 25 cannot return to the locking position. However, when the piercing tip 80 of the obturator 18 breaks through the body cavity wall and there is no resistance to the spring loaded shield 15, the shield 15 will spring completely forward to cover the piercing tip 80 and the pivoting chock 25 will pivot into its original locking position. In this fashion, once the body cavity wall has been pierced and the shield 15 has locked, the shield 15 cannot again retract to expose the piercing tip 80 unless the operating physician uses the trigger 48 to rearm the trocar 10. FIG. 2D shows a front sectional view of the latch means 33. Although the illustrated trigger 48 in FIG. 2A is mounted on the cannula 13, it is also possible to place the trigger 48 on the obturator 12 and utilize another guiding tab 60 in place of the linking member 24 to join the cannula 13 and obturator 12.

FIG. 3A shows the preferred latch means 33. The latch means 33 is substantially similar to that of FIG. 2A but provides enhanced locking and unlocking action. Specifically, the latch means 33 comprises a biasing means such as the leaf spring 27, a blocking member such as the illustrated pivoting chock 25, an actuation means such as the trigger 48, and a linkage between the actuation means and the blocking means such as the linking member 24. The illustrated latch means 33 operates to keep the shield 15 locked in the extended position except when armed or actuated. To lock the shield 15, a solid portion 30 of the pivoting chock 25 engages with a lug 32 on the proximal end 50 of the shield 15 to prevent the shield 15 from retracting further toward the inner wall 20 of the obturator housing 17 and thereby exposing the piercing tip 80.

In order to permit the shield 15 to be retracted, the latch means 33 must first be armed or actuated. In the embodiment illustrated in FIG. 3A, the distal end 22 of the linking member 24 engages with a trigger 48. When the trigger 48 is depressed and pushed forward toward the piercing tip 80, the linking member 24 is likewise pulled forward. A hook 29 on the proximate end of the linking member 24 is engaged in a cradle 28 on the pivoting chock 25. As the linking member 24 is pulled forward, it causes the pivoting chock 25 to turn on its pivot 26 and thereby rotates the solid portion 30 away from the lug 32 on the proximal end 50 of the shield 15. This arms or actuates the trocar 10.

The enhancement of the embodiment of FIG. 3A comprises a detent such as finger 76 which is adapted to be received in recess 75 of inner housing 39. When the trigger 48 is pushed sufficiently forward toward the piercing tip 80 to arm the trocar 10, biased finger 76 is pressed into recess 75 and acts to restrain further movement of the trigger 48 in either the forward or reverse directions. This has the effect of maintaining the trocar 10 in an actuated status without the necessity of continuing to exert manual forward pressure on the trigger 48. Biased finger 76 is preferably made of a slightly flexible and resilient material such as plastic and when the trigger 48 is manually urged in the reverse direction away from the piercing tip 80, finger 76 can be dislodged from recess 75 and the latch means 33 can be returned to its locked position. This allows the trocar 10 to be actuated and deactuated by merely sliding trigger 48. The arming mechanisms of prior art trocars usually require either that the shield be retracted to expose their pyramidal tips or that the obturator portion be disengaged from the cannula in order to relock an armed device. When properly employed, the latch means illustrated in FIG. 3A represents a significant safety improvement.

It should be pointed out that finger 76 and recess 75 in the preferred embodiment of FIG. 3A accomplish the same object as stop block 23 in FIG. 2A, namely, halting the forward movement of linking member 24 in close proximity to cam 31 protruding from the proximal end 50 of the shield 15. In FIG. 3A, as in FIG. 2A, when the surgeon applies pressure to the trocar 10, the shield 15 is pushed back into the housing 17. The cam 31 on the proximate end 50 and the shield 15 then dislodges the hook 29 of the linking member 24 from the cradle 28 of the pivoting chock 25. A biasing means such as the leaf spring 27 acting on the pivoting chock 25 now causes the solid portion 30 of the pivoting chock 25 to try to return to its original locking position. If the shield 15 is even partially retracted, the pivoting chock 25 cannot return to the locking position. However, when the piercing tip 80 of the obturator 18 breaks through the body cavity wall and there is no resistance to the spring loaded shield 15, the shield 15 will spring completely forward to cover the piercing tip 80 and the pivoting chock 25 will pivot into its original locking position. In this fashion, once the body cavity wall has been pierced and the shield 15 has locked, the shield 15 cannot again retract to expose the piercing tip 80 unless the operating physician uses the trigger 48 to rearm the trocar 10.

Referring again to FIG. 2A, the cannula 13 includes an outer housing 40, an inner housing 39, and a cannula tube 14 which is secured to and extends from the inner housing 39. In addition, as shown in FIGS. 2A, 3A, and 3C the inner housing 39 is mounted within the outer housing 40. The inner housing 39 contains a gas sealing means such as the illustrated flapper valve 41, comprised of a pivot arm 42 and a biased flapper 43. The flapper valve 41 will allow the introduction of the obturator sheath 18 of a shielded obturator 12, or other endoscopic instruments (not illustrated) without substantial loss of gas from the body cavity. As shown in FIG. 3C, when no instrument is inserted, the flapper 43 closes against the gasket 56 to maintain the gaseous pressure in the body cavity. In addition, a further gas sealing means such as the illustrated membrane seal 92 is positioned above the flapper valve 41 to provide further protection against loss of gas from the body cavity.

In its preferred embodiment as shown in FIGS. 2A and 3A, the proximal end 69 of the cannula tube 14 engages and locks with the inner housing 39. The inner housing 39 is preferably fabricated as one piece of plastic, or other suitable material, so that there are no seams which would require welding or other special sealing in order to be able to prevent excessive gaseous leakage and loss of pneumoperitoneum. A detailed view of the flapper valve 41 is shown in FIG. 2B which shows that the pivot arm 42 is inserted through an opening 53 in the inner housing 39, through an 0-ring 44 and into the flapper 43. A biasing means such as the spring 45 is engaged in a channel 54 in the exposed end 46 of the pivot arm 42. The outer housing 40 is then assembled around the inner housing 39. Finally, a lever arm 47 is attached to the exposed end 46 of the pivot arm 42. The lever arm 47 allows the surgeon to manually open the flapper 43 for tissue removal or in the event an endoscopic instrument of irregular shape is used that would otherwise not easily be inserted or removed by virtue of pressure from the biased flapper 43.

Because different types of operations require the use of endoscopic and laparoscopic instruments of various diameters, obturators are also made in a variety of diameters. The illustrated cannula 13 in FIG. 2A can easily be manufactured to accommodate a variety of obturator diameters by resizing only the diameter of the cannula tube 14 and guide member 38. All other components of the cannula 13 can be interchangeably used in the manufacture of trocars 10 of varying diameter.

Figure 2E:
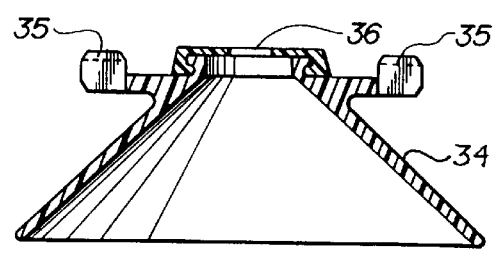
FIG. 2E illustrates a sectional side view of the funnel attachment shown in FIG. 2C.

Sometimes it is also desirable for a surgeon to use a large diameter obturator, of perhaps 10 mm, to make the incision, but use an instrument of much narrower diameter, of perhaps 5 mm, during a part of the surgical procedure. In order to prevent excessive leakage of gas and the concomitant risk of loss of the pneumoperitoneum when using an undersized instrument through the flapper valve 41, the invention illustrated in FIG. 2A is also provided with an optional funnel attachment 34 shown in FIGS. 2C and 2E. The funnel attachment 34 is sized to fit on the seating ring 37 of a larger guide member 38 and has a gas sealing means such as the illustrated membrane seal 36 sized for smaller instruments. The funnel attachment 34 also has mounting tabs 35 which may fit in the same openings 61 and 62 where tabs 22 and 60 of the shielded obturator 12 connect with the cannula 13. In this fashion, even though the smaller instrument creates a gap allowing the flow of gas through the flapper valve 41, the seal 36 of the funnel attachment 34 prevents loss of the pneumoperitoneum.

Also shown in FIGS. 1 through 3 is a helically wound thread 49 on the outer surface of the cannula tube 14. As shown in FIGS. 3A and 3C, the helically wound thread 49, preferably begins at a reduced height a short distance from the distal end 68 of the cannula tube 14 and gradually increases to its full height and proceeds for a distance toward the proximate end 69 of the cannula tube 14 which connects with the inner housing 39. The side 66 of the helical thread 49 facing the distal end 68 of the cannula tube 14 is backward sloping, while the opposed side 67 of the helical thread 49 facing the proximate end 69 of the cannula tube 14 is substantially perpendicular to the surface of the cannula 14.

As previously stated, the shielded obturator 12 and cannula 13 are interfitting. In FIG. 2A, the distal end 22 of the linking member 24 from the shielded obturator 12 is received through opening 62 and engaged in the trigger 48 mounted in the cannula 13. Also a guiding tab 60 from the shielded obturator 12 is received in an opening 61 in the cannula 13. In an alternative embodiment shown in FIGS. 3A, 3B and 3C, the guiding tab 60 and the distal end 22 of the linking member 24 from the shielded obturator 12 are interlockingly received in openings 61 and 62 respectively of the cannula 13. By depressing push buttons 63 and 64, the guiding tab 60 and linking member 24 can be disengaged, allowing for easy separation of the shielded obturator 12 from the cannula 13.

Of particular importance is that depressing push button 64 presses on linking member 24 and thereby dislodges the distal end 22 of linking member 24 from engagement with trigger 48. Thus, when push button 64 is depressed to separate the obturator 12 from the cannula 13, the latch means 33 will automatically return to its locked position as shown in FIG. 3B. This prevents accidental retracting of the shield 15 when the obturator 12 is separated from the cannula 13 after being used to penetrate a body cavity wall and contributes to greater operating room safety.

Figure 4A:
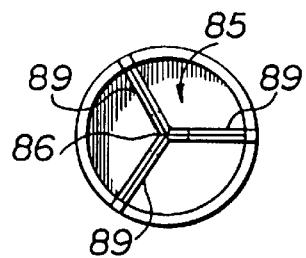
FIG. 4A illustrates a back plan view of an embodiment of a piercing tip for the invention.
Figure 4C:
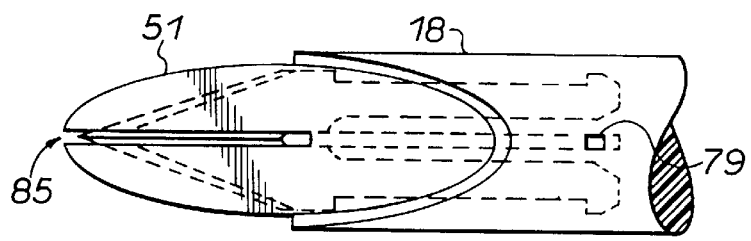
FIG. 4C illustrates a side plan view of the piercing tip shown in FIG. 4A mounted in an obturator sheath with a shield in its extended protective position.
Figure 4B:
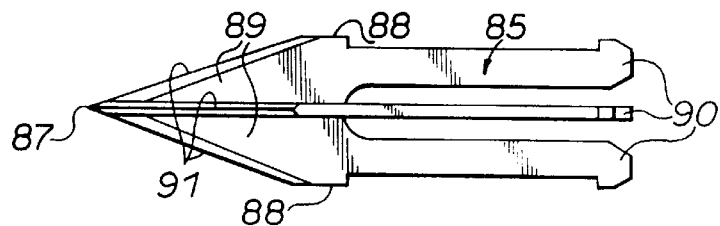
FIG. 4B illustrates a side plan view of the piercing tip shown in FIG. 4A.

FIGS. 4A and 4B are an illustration of an embodiment of a piercing tip 85 comprised of three pointed blades 89. Each pointed blade 89 is joined along a central axis 86 and proceeds from a distal end 87 of the piercing tip 85 along a straight sharpened edge 91 down to a shoulder 88. The illustrated piercing tip 85 has three struts 90 which are received and locked within openings 79 (shown in FIG. 4C) in the obturator sheath 18.

Figure 5B:
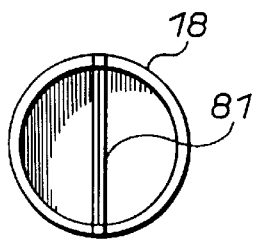
FIG. 5B illustrates a back plan view of the piercing tip shown in FIG. 5A.
Figure 5C:
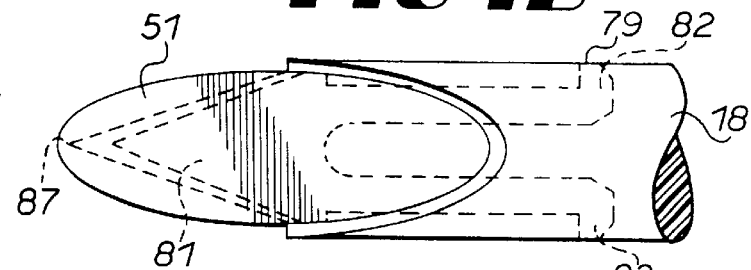
FIG. 5C illustrates a top plan view of the piercing tip shown in FIG. 5A mounted in an obturator sheath the shield in its extended protective position.
Figure 5A:
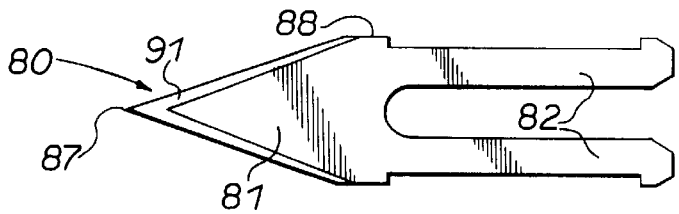
FIG. 5A illustrates a top plan view of another embodiment of a piercing tip for the invention.

FIGS. 5A, 5B and 5C illustrate the presently preferred embodiment of the piercing tip 80, which is comprised of a pointed blade 81. The illustrated pointed blade 81 is substantially planar and has a central pointed distal end 87 and straight sharpened edges 91 proceeding from both sides of said distal end 87 to the shoulders 88. In alternative constructions, the blade 81 may have slight convex or concave curve to the sharpened edges 91. The point of the blade may be acute as illustrated or rounded. Other variations of a pointed blade or blades may also be utilized. Extending rearwardly from the blade portion 81 are shown two struts 82 which are received and locked within openings 79 (shown in FIG. 5C) in the obturator sheath 18. If the obturator 12 is to be reused, the struts 82 may be dislodged from the openings 79 so that the piercing tip 80 may be removed after use and sharpened or replaced with a new piercing tip 80.

Figure 5D:
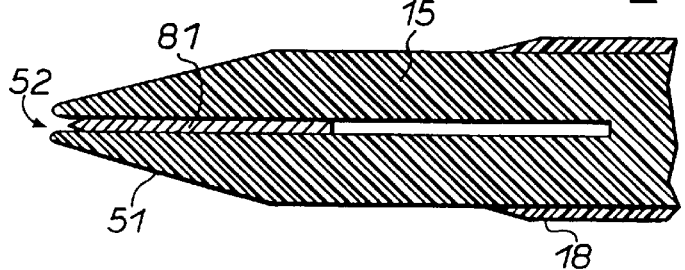
FIG. 5D illustrates a sectional side plan view of the piercing tip shown in FIG. 5A mounted in an obturator sheath with a shield in its extended protective position.

FIG. 5D illustrates the shield 15 designed for use with the piercing tip 80 shown in FIGS. 5A through 5C. The shield 15 is preferably cylindrical in form to fit within the obturator sheath 18. The blunt distal end 51 of the shield 15 has a channel 52 of a width sufficient to receive the pointed blade 81 when the shield 15 is in its extended position.

Figure 6A:
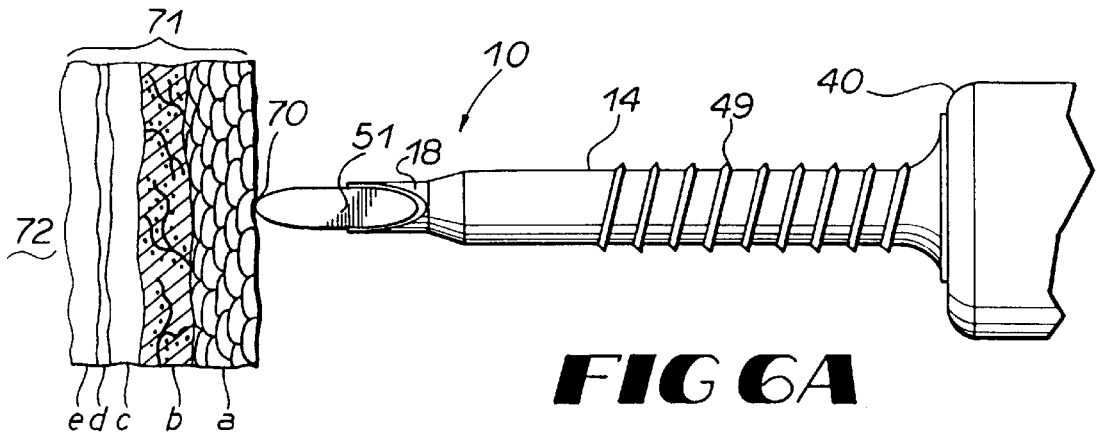
FIGS. 6A through 6D show, in sequential diagrammatic sectional views, an embodiment of the present invention as used to puncture a body cavity wall of a patient.

FIGS. 6A through 6D illustrate the piercing tip 80 and shield 15 of the trocar 10 in use. In FIG. 6A, a small incision 70 is made in the surface of the skin or epidermis "a" of the body cavity wall 71 of a patient. This incision helps both to position the piercing tip 80 of the trocar 10, and also reduces slightly the pressure required to penetrate the body cavity wall by penetrating the epidermis. A particular advantage of the pointed blade 81 of the present invention is that the step of making a preliminary incision is rendered unnecessary because the pointed blade 81 positions itself accurately where urged into contact with the epidermis "a" and because the pointed blade 81 can more easily penetrate a body cavity wall than a traditional pyramidal tip.

Figure 6B:
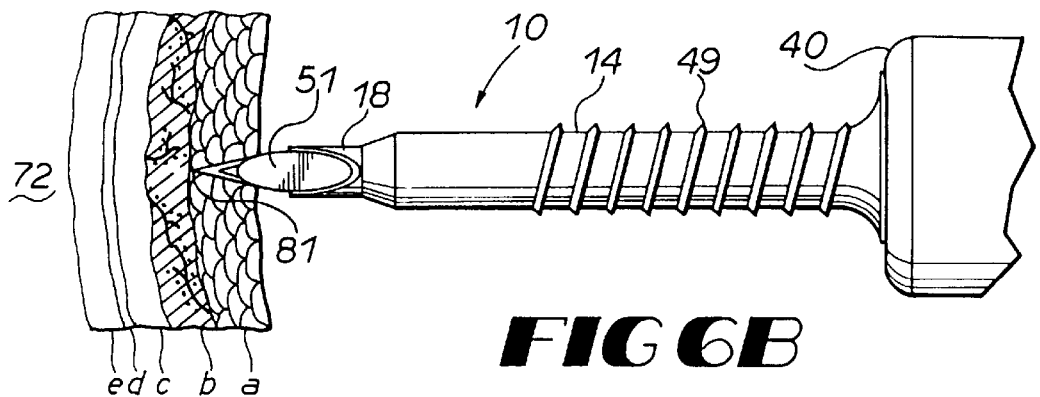

The piercing tip 80, in this case the pointed blade 81, of the trocar 10 with extended shield 51 may then be placed against the incision 70 as shown. When the trocar 10 is in this position, it may be armed or actuated by depressing the trigger 48 (shown in FIGS. 2A and 3A) and sliding the trigger 48 forward as explained above. When manual force is applied to the obturator housing 17 which forms the trocar handle (shown in FIG. 2A) pushing the trocar to the left, the resistance of the body cavity wall 71 holds back the distal end 51 of the shield 15 and the pointed blade 81 is exposed as shown in FIG. 6B. The pointed blade 81 then slices through the dermis "a" and subcutaneous tissue including fat cells, muscle, and facia, depicted as "b," "c," "d" and "e" in FIGS. 6A–6D. The various layers of the body cavity wall 71 vary depending upon the cavity being pierced, but in general, the layers of facia are particularly resistant to penetration.

Figure 6C:
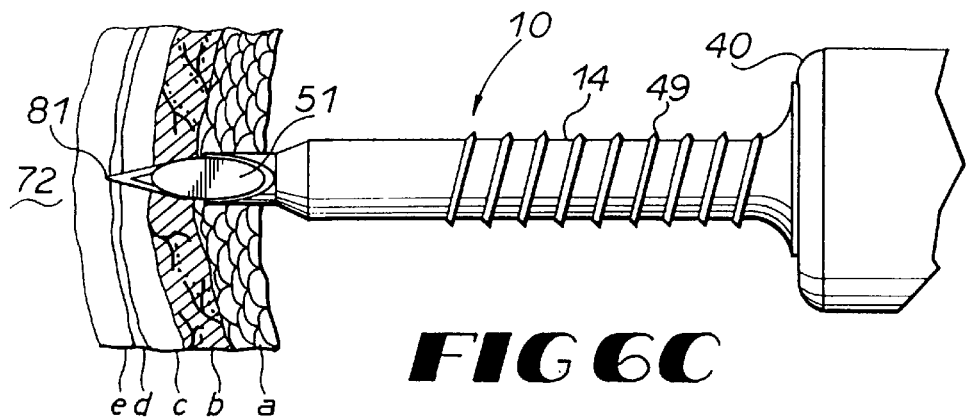

In FIG. 6C, even before the pointed blade 81 has completely penetrated the innermost layer "e" of the body cavity wall 71, the distal end 51 of the shield 15 is forced forward into the incision 70 by the bias of the coil spring 21. The bias provided by the coil spring 21 is of such force that in the preferred embodiment, the blunt distal end 51 of the shield 15 may enter an incision 70 with a length less than the diameter of the shield 15 and may stretch or tear the body cavity wall 71 adjacent to the incision 70 to accommodate passage of the shield 15 through the incision 70.

Figure 6D:
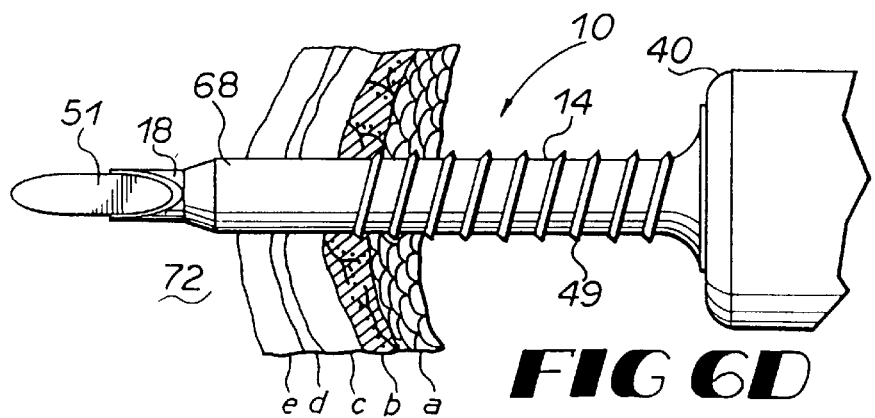

FIG. 6D shows that the shield 15, the obturator sheath 18, and the distal end 68 of the cannula tube 14 all proceed through the incision 70 in the body cavity wall 71 as manual force continues to be applied to the trocar 10. Just as the blunt distal end 51 of the shield 15 passes through the inner layer "e" of the body cavity wall 71, the resistance of the body cavity wall 71 is significantly reduced and the shield 15 is pushed to its fully extended position with the distal end 51 covering the pointed blade 81. This action protects the interior of the body cavity 72 immediately after the penetration of the pointed blade 81 through the body cavity wall 71 and protects organs, blood vessels and other anatomical structures from incidental contact with the blade 81 or of the trocar 10. Simultaneously with the full extension of the shield 15 into its protective position covering the pointed blade 81, the pivoting chock 25 engages the lug 32 on the proximate end 50 of the shield 15, which prevents the shield 15 from being retracted to expose the pointed blade 81 until the trocar 10 is again actuated by depressing and moving the trigger 48 forward.

Figure 8:
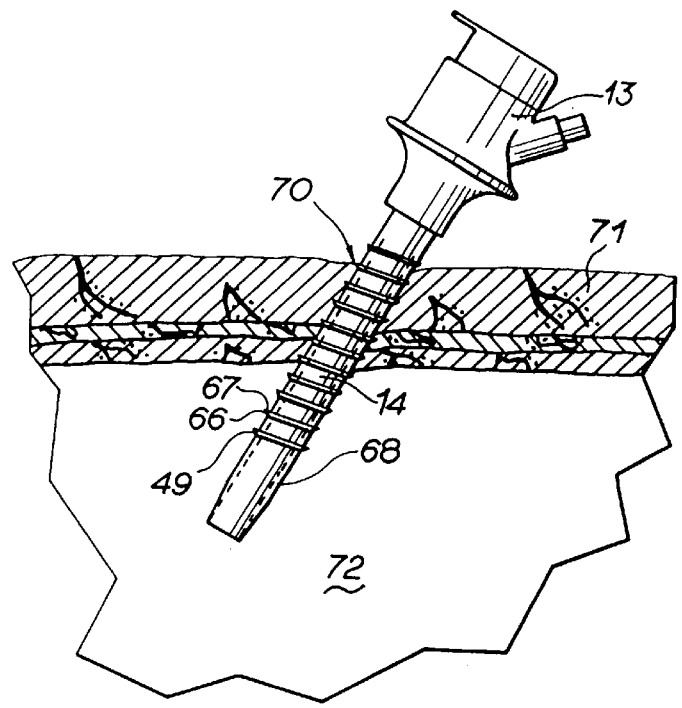
FIG. 8 is a sectional view of a body cavity wall with the cannula of FIG. 7B inserted through an incision.

Turning now to FIG. 8, once the distal end 68 of the cannula tube 14 has entered the incision 70, the shielded obturator 12 may be removed. The cannula 13 may also be inserted further through the body cavity wall 71 to the desired depth. Unlike previous threaded cannulas, when the backward sloping sides 66 of the helical threads 49 come into contact with the edges of the incision 70, the present improved cannula 13 need not be rotated to thread the cannula tube 14 into the incision 70. As shown in FIG. 8, the backwardly sloping distal edges 66 of the helically wound thread 49 allow the cannula tube 14 to be directly inserted to the desired depth. The perpendicular proximal edges 67 of the thread 49 hold the cannula 13 securely in place. When the surgical procedure is completed, the cannula 13 may be easily removed by rotating it in a counterclockwise direction. Because the incision made by a planar pointed blade 81 is only a single slit the width of the inner diameter of the cannula, when the threaded cannula is inserted into the incision, it is firmly gripped by the surrounding body cavity wall almost uniformly providing a substantially air tight seal between the cannula and body cavity wall. In contrast, a traditional pyramidal piercing tip leaves a puncture-type wound with at least three cuts or tears in the body cavity wall radiating from the central entry point of the piercing tip. These cuts or tears delimit separate flaps of tissue that do not tightly grip a cannula inserted into the puncture.

Figure 7A:
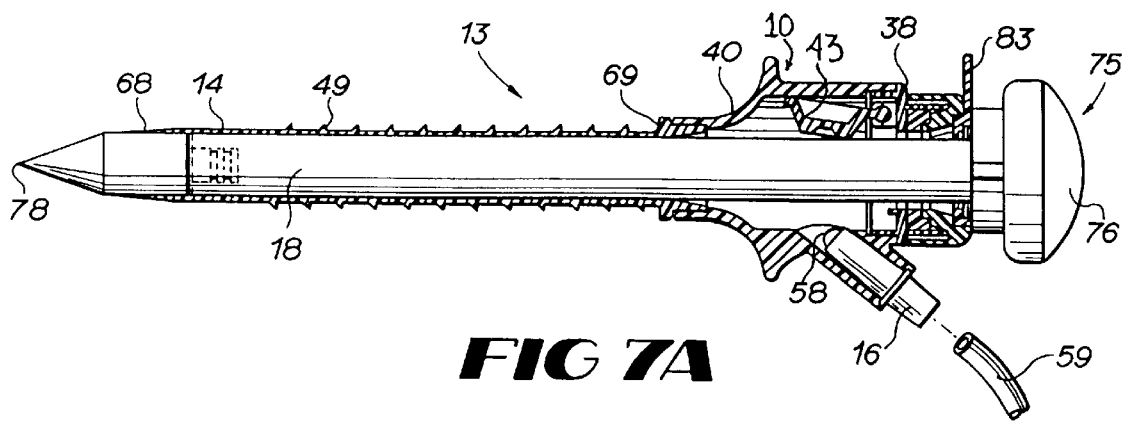
FIG. 7A illustrates a side plan view of an alternative embodiment of an improved cannula in cross-section according to the present invention with an interfitting obturator of traditional design.

FIG. 7A shows another embodiment of an improved cannula 13 with an interfitting traditional obturator 75 having an obturator sheath 18 fitted with a piercing tip 78 of either pyramidal or conical shape. This cannula 13 also may be used with the improved shielded obturator 12 (shown in FIGS. 2A and 3A) previously described. The proximate end of the traditional trocar 75 is fitted with a knob or handle 76 to provide a surface on which the palm of the surgeon's hand may be pressed. The helically wound thread 49 is shown beginning adjacent to the distal end 68 of the cannula tube 14 and gradually increasing to full height and proceeding toward the proximate end 69 of the cannula tube 14. The distal side 66 of the thread 49 is backward sloping and the opposite proximal side 67 of the helical thread 49 is substantially perpendicular to the cannula tube 14. The proximal end 69 of the cannula tube 14 fits into the outer housing 40 in such a fashion that during assembly, cannula tubes 14 of varying diameter may be mounted to an outer housing 40 of uniform size and construction. For instance, a cannula tube 14 of lesser inner diameter as shown in FIG. 7D has a proximal end 69 of the same outer diameter and can be mounted in the same outer housing 40 as the cannula tube 14 of larger inner diameter in FIG. 7A.

Figure 7B:
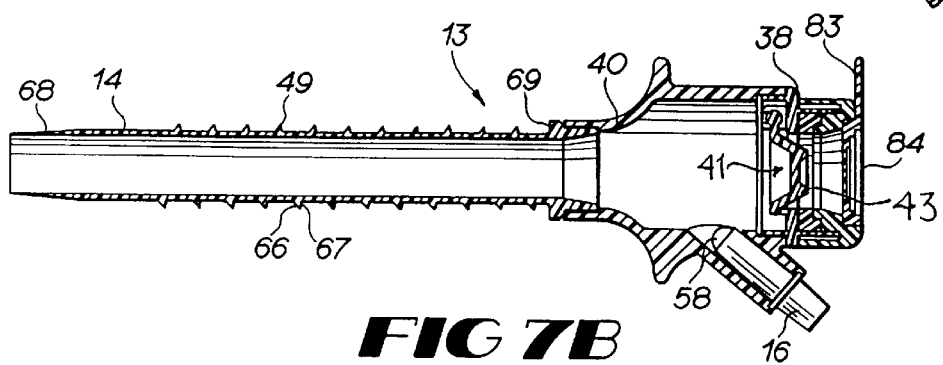
FIG. 7B illustrates a sectional side plan view of the cannula of FIG. 7A in isolation, and the flapper valve is shown in its closed position.

FIG. 7B illustrates the same cannula 13 as was shown in FIG. 7A, but in isolation from the interfitting traditional obturator 75. Also, because the traditional obturator 75 is removed, the biased flapper 43 of the flapper valve 41 of the cannula 13 has returned to its closed position. Another feature of the improved cannula 13 is the illustrated spring depression valve 16 for the introduction of a gas supply to maintain the pneumoperitoneum. This spring depression valve 16 is comprised of an internal Luer-Lok fitting or a bayonet fastener or quarter turn fastener, (all as known in the art and not shown) to engage the tube 59 from the gas supply, and a gate 58 which is opened upon insertion of the gas supply tube 59. In this fashion, it is not necessary to open and close any valves on the trocar 10 when using a gas supply tube 59 to maintain pressure in the body cavity.

Figure 7C:
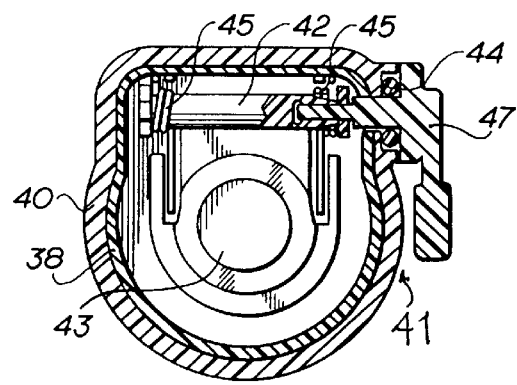
FIG. 7C illustrates a top sectional view of the flapper valve assembly of the cannula illustrated in FIG. 7B.

FIG. 7C illustrates the flapper valve 41 of the cannula 13 of FIG. 7A and 7B in greater detail. Illustrated are the flapper 43 on pivot arm 42, biasing means such as the springs 45, the lever arm 47 for manually opening the flapper valve 41, and an o-ring 44 to seat the lever arm 47 and to seal against gas leakage. Also shown is a snap fitting guide member 38 set inside the housing 40.

Figure 7D:
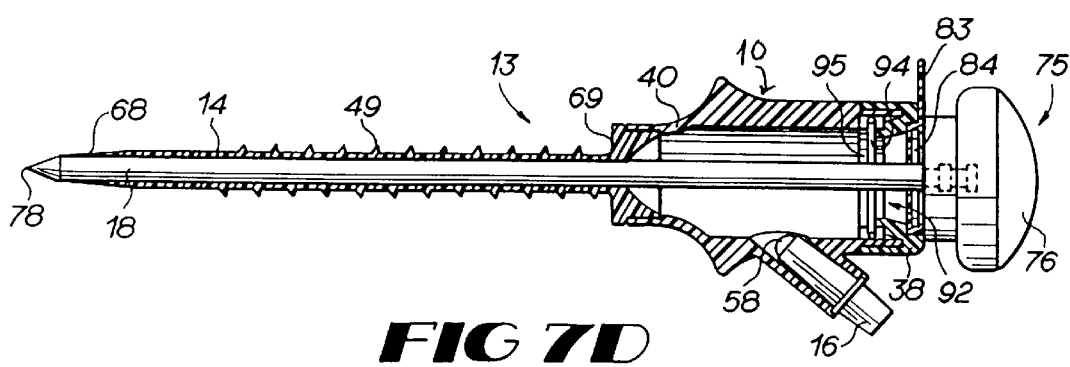
FIG. 7D illustrates a side plan view of an improved cannula in cross-section similar to that shown in FIG. 7A with an interfitting obturator of traditional design, but adapted for use with an obturator of smaller diameter and utilizing a membrane seal rather than a flapper valve.

FIG. 7D illustrates a narrow diameter version of the cannula 13 shown in FIG. 7A and 7B. Aside from the narrower diameter cannula tube 14, this embodiment also shows the replacement of the flapper valve 41 with an alternative gas sealing means, namely a membrane seal 92.

Figure 9:
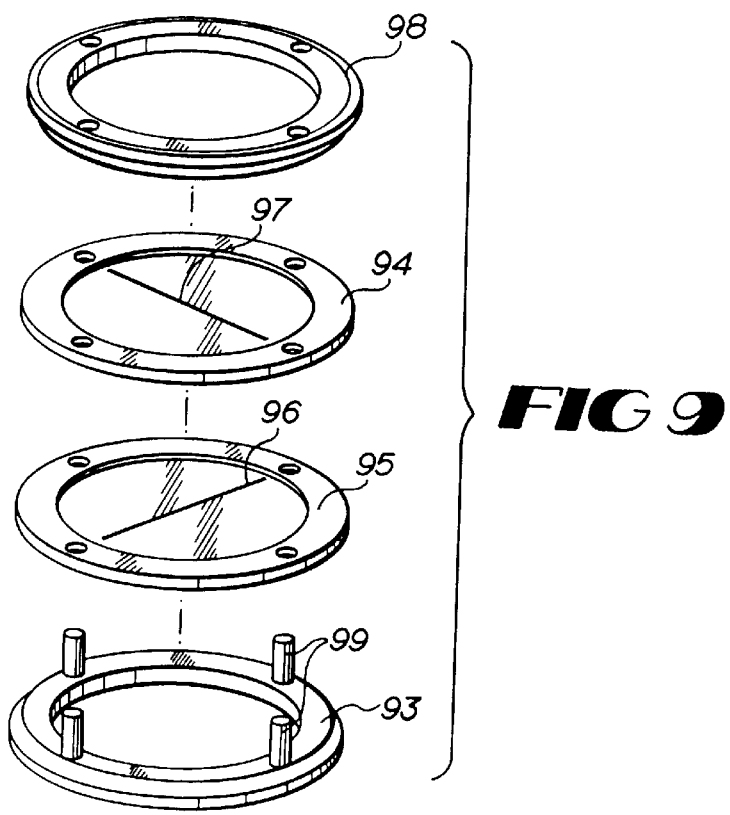
FIG. 9 is an exploded perspective view of the membrane seal utilized on the cannula illustrated in FIG. 7D.

The membrane seal 92 is illustrated in greater detail in FIG. 9 and is comprised of an upper membrane 94 with an upper membrane central slit 97 of length approximately equal to the diameter of the cannula tube 14 with which it is to be used. The membrane seal 92 is further comprised of a lower membrane 95 having a lower membrane central slit 96 of the same length but mounted so that the lower membrane central slit 96 is at right angles to the upper membrane central slit 97. The upper and lower membranes 94 and 95 are stacked on a base 93 with mounting posts 99 and capped with a mounting ring 98.

Another feature shown in FIG. 7B is a reducing fitting such as the illustrated snap-on reducing fitting 83. This snap-on reducing fitting 83 has a gas sealing means such as the membrane seal 84 through which the obturator sheath 18 or an endoscopic or laparoscopic instrument (not illustrated) may be inserted. In the event that instruments of smaller diameter than the obturator sheath 18 are used, an appropriate snap-on reducing fitting 83 may be selected so that a good fit is maintained between the membrane seal 84 and the instrument, and there will not be excessive loss of gas. If desired, the reducing fitting may be equipped with a double membrane seal of the type illustrated in FIG. 9.

Numerous alterations of the structure herein described will suggest themselves to those skilled in the art. It will be understood that the details and arrangements of the parts that have been described and illustrated in order to explain the nature of the invention are not to be construed as any limitation of the invention. All such alterations which do not depart from the spirit of the invention are intended to be included within the scope of the appended claims.

We claim:

1. A shielded trocar comprising:
   (a) a shielded obturator having a proximal end comprising a handle and having a distal end comprising a piercing tip;

(b) a cannula with a housing and a cannula tube, the cannula tube having a lumen of sufficient diameter to receive the piercing tip of the obturator;

(c) a shield slidably mounted relative to the piercing tip of the obturator and movable between an extended protective position and a retracted unprotective position;

(d) a biasing means tending to bias the shield into the extended protective position;

(e) a latch operatively connected to said obturator and having a first position permitting the shield to be locked in the extended protective position, and having a second position permitting the shield to slide from its extended protective position towards its retracted unprotected position when force is applied to said shield;

(f) said latch being adjustable both between said first position and said second position, and between said second position and said first position without moving the shield relative to said cannula.

2. The trocar of claim 1 wherein the latch is biased to automatically resume the first locking position upon return of the shield to the extended protective position after having been forced toward its retracted unprotected position.

3. The trocar of claim 1 wherein the latch is comprised of a biasing means, a blocking member, a trigger, and a detent.

4. The trocar of claim 3 wherein the detent is adapted to releasably secure the latch in its second position permitting the shield to slide from its extended protective position towards its retracted unprotected position when force is applied to said shield.

5. The trocar of claim 4 wherein the piercing tip comprises a substantially planar pointed blade.

6. The trocar of claim 3 wherein the piercing tip comprises a substantially planar pointed blade.

7. The trocar of claim 1 wherein the piercing tip comprises a substantially planar pointed blade.

8. The trocar of claim 1 wherein the shielded obturator further comprises an obturator sheath having a proximal end mounted to the handle and having a distal end supporting the piercing tip.

9. The trocar of claim 1 wherein the latch is forced into its first position permitting the shield to be locked in the extended protective position whenever the shielded obturator is removed from the cannula.

10. A shielded trocar according to claim 1 wherein said shielded obturator further comprises a linking member engaging with the cannula when the cannula and obturator are interfitting and wherein said latch is adjustable both between said first position and said second position, and between said second position and said first position while the linking member of said obturator is engaged with said cannula.

11. The trocar of claim 10 wherein the latch is biased to automatically resume the first locking position upon return of the shield to the extended protective position after having been forced toward its retracted unprotected position.

12. The trocar of claim 10 wherein the latch is comprised of a biasing means, a blocking member, a trigger, and a detent.

13. The trocar of claim 12 wherein the detent is adapted to releasably secure the latch in its second position permitting the shield to slide from its extended protective position towards its retracted unprotected position when force is applied to said shield.

14. The trocar of claim 13 wherein the piercing tip comprises a substantially planar pointed blade.

15. The trocar of claim 12 wherein the piercing tip comprises a substantially planar pointed blade.

16. The trocar of claim 10 wherein the piercing tip comprises a substantially planar pointed blade.

17. The trocar of claim 10 wherein the shielded obturator further comprises an obturator sheath having a proximal end mounted to the handle and having a distal end supporting the piercing tip.

18. The trocar of claim 10 wherein the latch is forced into its first position permitting the shield to be locked in the extended protective position whenever the shielded obturator is removed from the cannula.

19. A shielded trocar comprising:

(a) a cannula with a housing, and a cannula tube having a lumen, a trigger, and a detent;

(b) a shielded obturator having a proximal end comprising a handle and a distal end comprising a piercing tip, said piercing tip being received within the lumen of the cannula tube so that the cannula and obturator are interfitting;

(c) a shield having a proximal end received in the obturator handle and a distal end slidably movable relative to the piercing tip between an extended protective position covering the piercing tip and a retracted, unprotected position exposing at least a portion of the piercing tip;

(d) a biasing means tending to bias the shield into the extended, protective position;

(e) a blocking member contained in the handle and having a first blocking position which prevents the shield from moving toward the retracted position and a second unblocked position which allows the shield to move towards the retracted position in response to pressure;

(f) a biasing means tending to push the blocking member into its first blocking position; and (g) the trigger on the cannula having a proximal end in communication with the blocking member when the cannula and obturator are interfitting and a distal end having a finger, said trigger being slidable between a first position which allows the blocking member to remain in its first blocking position, and a second position which moves the blocking member into its second unblocked position, the trigger being held in its second position by the finger releasably engaging with the detent, and whereby, the movement of said trigger from its first position to its second position permits the shield to be retracted toward the unprotected position in response to pressure, and the movement of said trigger from its second position to its first position causes the shield to be locked in the extended protective position, when the obturator is engaged with the cannula and without retracting the shield from the unprotected position.

* * * * *